United States Patent

Landis et al.

[11] Patent Number: 5,931,171
[45] Date of Patent: Aug. 3, 1999

[54] DENTAL FLOSSING APPARATUS

[75] Inventors: Timothy J. Landis, Loomis; Clay D. Allen, Elk Grove, both of Calif.

[73] Assignee: OP-D-OP, Inc., Roseville, Calif.

[21] Appl. No.: 09/115,411

[22] Filed: Jul. 14, 1998

[51] Int. Cl.⁶ .................................................. A61C 15/00
[52] U.S. Cl. ............................................................. 132/323
[58] Field of Search .................................. 132/323, 327, 132/324, 309, 326

[56] References Cited

U.S. PATENT DOCUMENTS

| | | | |
|---|---|---|---|
| 3,474,799 | 10/1969 | Cappello | 132/323 |
| 3,828,804 | 8/1974 | Ely | 132/323 |
| 3,835,872 | 9/1974 | Daniel | 132/324 |
| 4,016,892 | 4/1977 | Chodorow . | |
| 4,206,774 | 6/1980 | Griparis . | |
| 4,802,752 | 2/1989 | Chodrow . | |
| 4,827,952 | 5/1989 | Kos | 132/323 |
| 5,067,503 | 11/1991 | Stile | 132/324 |
| 5,105,840 | 4/1992 | Giacopuzzi | 132/326 |
| 5,388,600 | 2/1995 | Hart | 132/323 |
| 5,538,023 | 7/1996 | Oczkowski et al. | 132/323 |
| 5,560,378 | 10/1996 | Tiphonnet . | |
| 5,664,592 | 9/1997 | Regnier | 132/323 |

FOREIGN PATENT DOCUMENTS 2450603  11/1980  France ..................... 132/324

OTHER PUBLICATIONS

Flossmate Dental Floss Handle, Butler G–U–M, John O. Butler Company, Chicago, Il,Undated.

Primary Examiner—Todd E. Manahan
Attorney, Agent, or Firm—John P. O'Banion

[57] ABSTRACT

A dental flossing apparatus adapted to use dental floss having gripper elements. The apparatus includes a handle having a pair of arcuate prongs extending therefrom, a pair of receptacles defined within the handle and disposed adjacent the proximal end of each prong, and a pair of channels, wherein each channel extends from a receptacle towards the tip of the prongs. The tips are spaced apart such that a piece of dental floss can be stretched therebetween, and the receptacles are adapted and configured to securely hold each gripper element at the ends of the dental floss. As an alternate embodiment, a pair of handles are pivotally attached such that the distance between the tips of the prongs is variable based on the position of the handles relative to each other.

15 Claims, 6 Drawing Sheets

DENTAL FLOSSING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This application pertains generally to dental hygiene and more particularly to an apparatus for flossing teeth.

2. Description of the Background Art

Dental flossing is an often unpleasant but necessary routine for good oral hygiene. The conventional method for flossing teeth typically involves grasping opposite ends of a length of dental floss with each hand, and manually manipulating the floss back and forth between the teeth. Anyone who has performed this arduous, but necessary, task is well aware that the nature of dental floss inherently makes it difficult to securely grasp and tautly hold a tensioned strand while maneuvering and manipulating the suspended section between all the teeth in an effort to floss. The smoothness of the floss, in addition to the saliva, prevents the fingers and hand from getting a secure grip, and the ends of the floss is usually wrapped around the fingers to maintain tautness. Those who have flossed in this conventional manner are aware that a tightly wrapped finger is uncomfortable, if not downright painful. Such inconvenience and difficulties spurred the development of various means to hold the dental floss while flossing between the teeth.

One such means is a mechanical dental floss holder of the type which typically suspends a section of dental floss tautly across a pair of prongs whereby the suspended section of floss is used to floss between teeth. The prongs are attached to a handle, and the suspended floss section is supplied from a spool or roll of dental floss attached in some manner onto the flosser apparatus, thus providing a continuous supply until the entire roll or spool is exhausted.

Another such means is to attach stub sections or gripper handles at both ends of a short section of dental floss so that the gripper handles provide a finger grip on the piece of floss to facilitate flossing. This is taught in U.S. Pat. No. 4,016,892, which is incorporated herein by reference.

BRIEF SUMMARY OF THE INVENTION

By way of example and not of limitation, the present invention is a dental floss holder that is structured and configured to use dental floss sections that have gripper handles at each end, such as those taught in U.S. Pat. No. 4,016,892. The dental floss holder generally comprises a handle, a pair of spaced-apart prongs extending from the handle, a pair of receptacles for receiving gripper handles on dental floss, and channels extending along the prongs from the receptacles to the tips of the prongs for receiving dental floss. In use, the dental floss is attached to the invention wherein each gripper handle is held by a receptacle and the dental floss is threaded along each channel and between the tips of the prongs. The dental floss is suspended tautly between the tips of each prong where it can be used to floss between the teeth.

An object of the invention is to provide a dental floss handle to facilitate flossing between the teeth.

Another object of the invention is to provide a dental floss handle capable of using short sections of dental floss that have gripper handles at each end.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
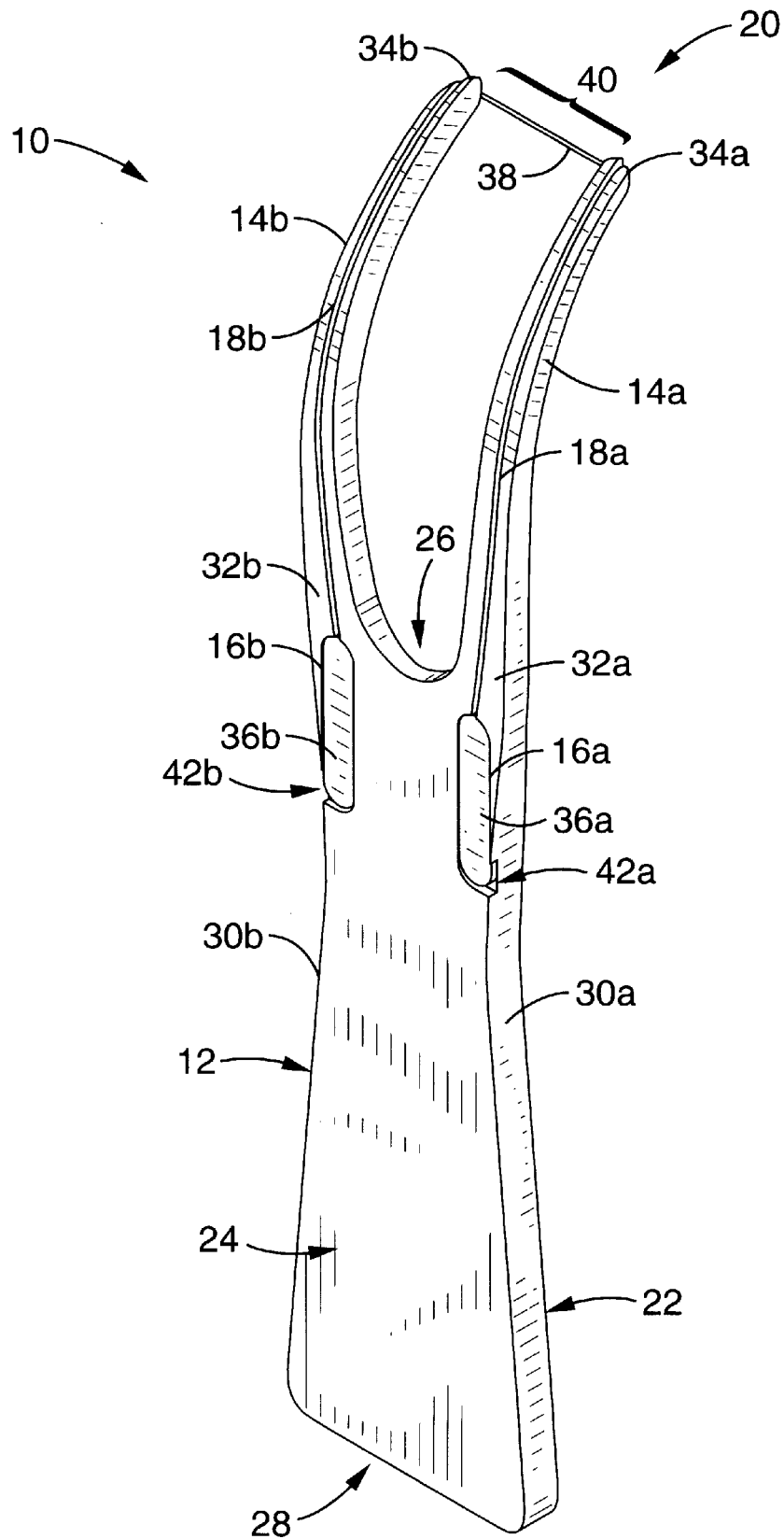
FIG. 1 is a perspective view of a dental flossing apparatus in accordance with the present invention showing the dental floss installed.
Figure 2:
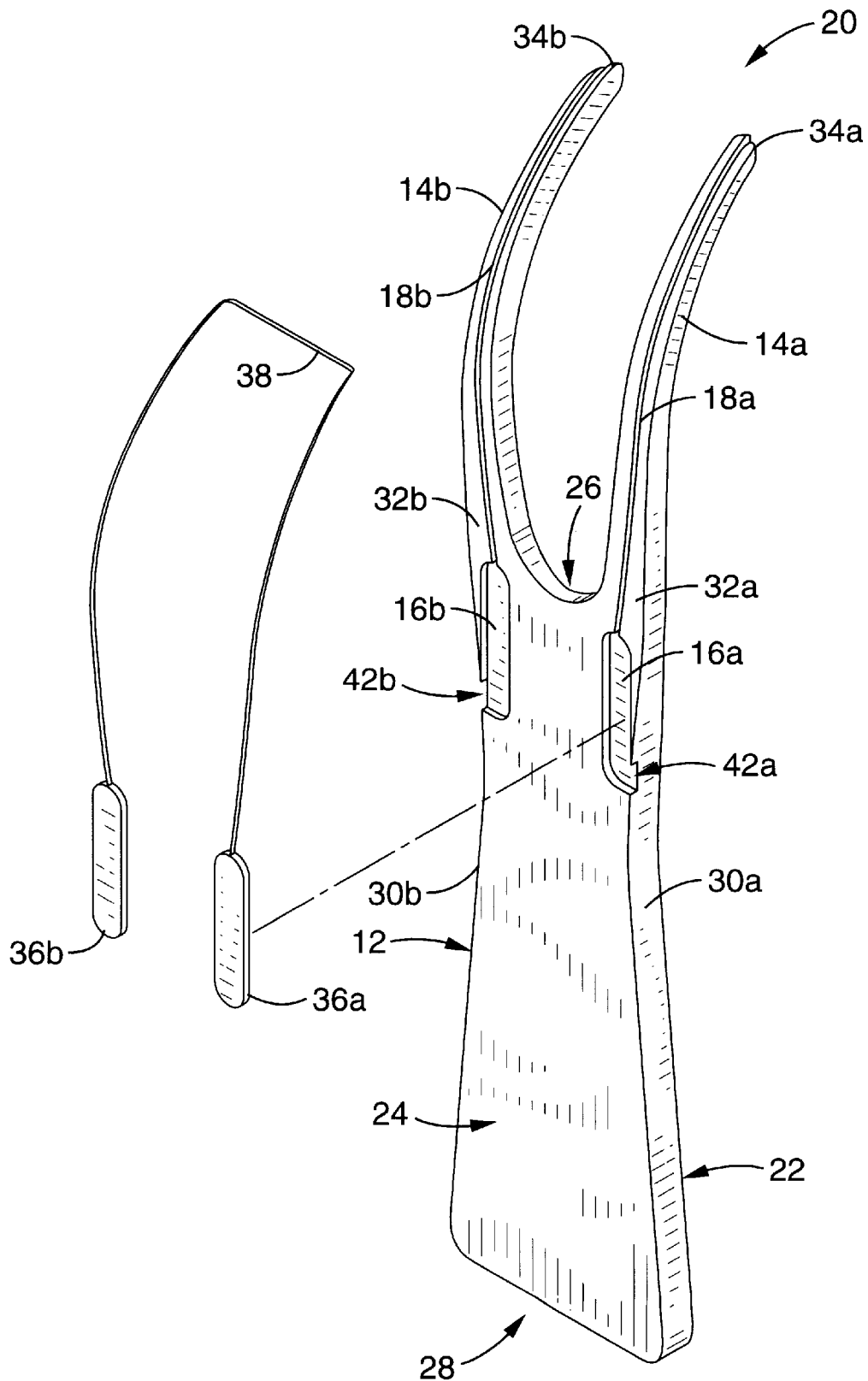
FIG. 2 is a perspective view of the dental flossing apparatus of FIG. 1 showing the dental floss removed.
Figure 3:
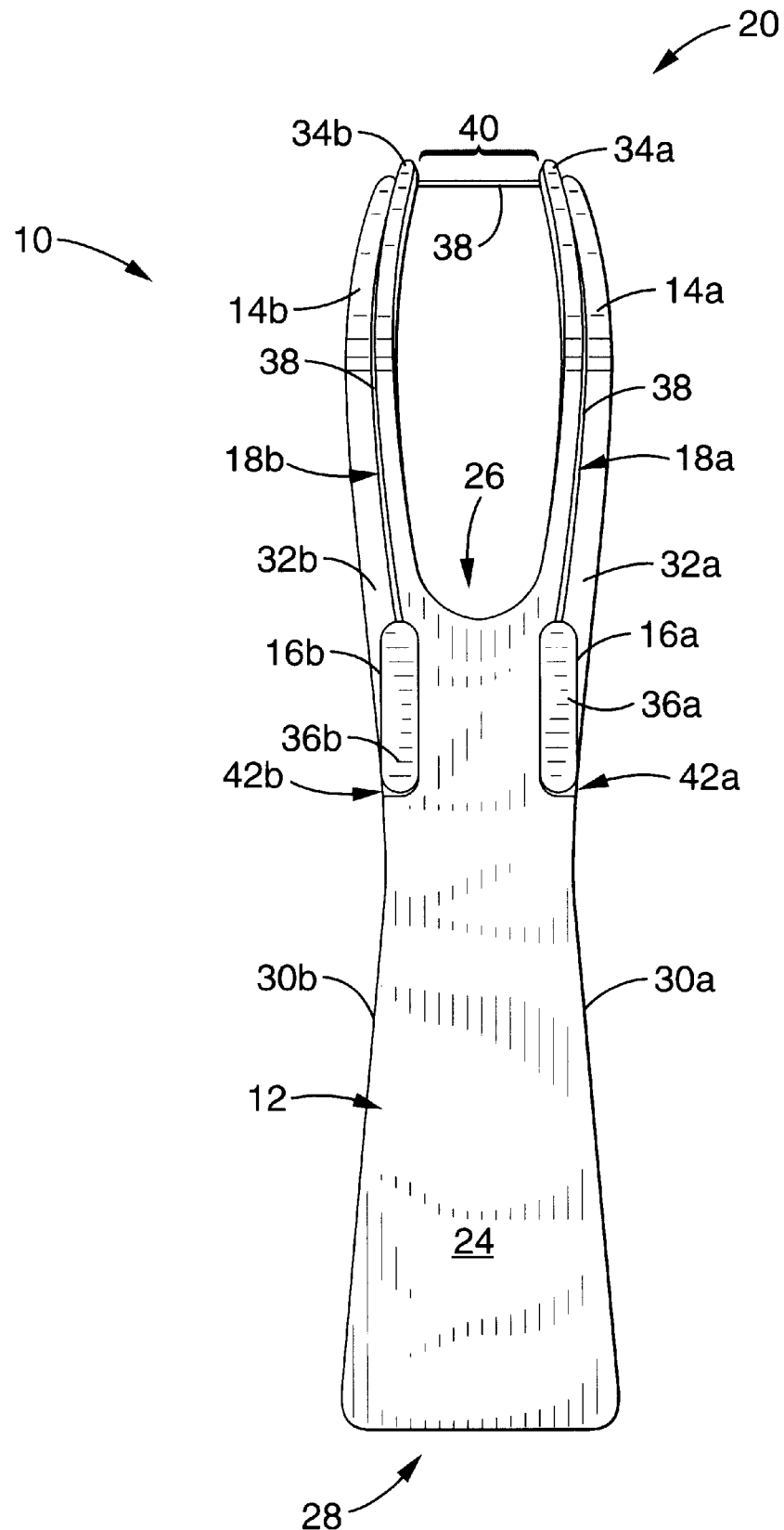
FIG. 3 is a top plan view of the dental flossing apparatus of FIG. 1 showing the dental floss installed.
Figure 4:
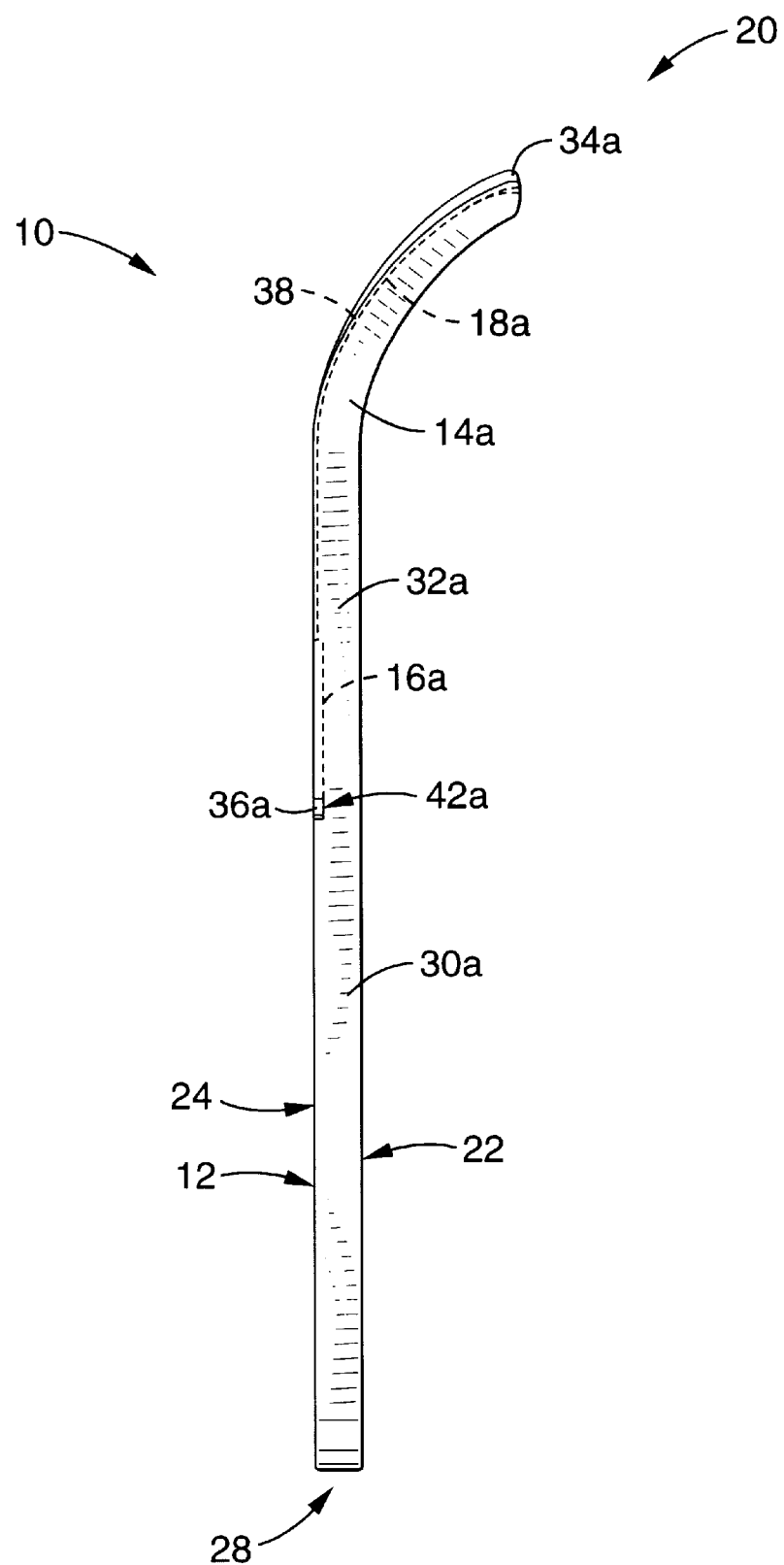
FIG. 4 is a side elevational view of the dental flossing apparatus shown in FIG. 1.

Referring more specifically to the drawings, for illustrative purposes the present invention is embodied in the apparatus generally shown in FIG. 1 through FIG. 4, where like reference numbers denote like parts. It will be appreciated that the apparatus may vary as to configuration and as to details of the parts without departing from the basic concepts as disclosed herein.

Referring to FIG. 1 through FIG. 4, a dental flossing apparatus 10 in accordance with the present invention is generally shown. The apparatus comprises a handle 12, first and second prongs 14a, 14b, respectively, extending from the handle, first and second receptacles 16a, 16b, respectively, and first and second channels 18a, 18b, respectively. Handle 12 preferably has face 22, a back face 24, a distal end 26, a proximal end 28, a first edge 30a and a second edge 30b. First and second edges 30a, 30b of handle 12 are preferably tapered and/or rounded to better conform to the palm of a user's hand and to provide a better grip thereon.

First and second prongs 14a, 14b each have a proximal end 32a, 32b, respectively, and a tip 34a, 34b, respectively, at the distal end 20 of the apparatus. Proximal ends 32a, 32b of prongs 14a, 14b are attached to distal end 26 of handle 12 and extend therefrom terminating at distal tips 34a, 34b. Receptacles 16a, 16b are typically elongated with each receptacle 16a, 16b disposed adjacent distal end 26 of handle 12 near proximal ends 32a, 32b of prongs 14a, 14b. Receptacles 16a, 16b are structured and configured to receive gripper handles 36a, 36b, respectively, which are affixed at each end of a section of dental floss 38, such as that shown in U.S. Pat. No. 4,016,892. Those skilled in the art will appreciate that receptacles 16a, 16b are not limited in shape but can be configured in any like manner to conform to whatever shape gripper handles 36a, 36b may take. In addition, it will be appreciated that receptacles 16a, 16bcould alternatively be located on prongs 14a, 14b, respectively. First channel 18a extends along first prong 14a from receptacle 16a to tip 34a. Similarly, second channel 18b extends along second prong 14b from receptacle 16b to tip 34b.

The apparatus can be fabricated from a variety of materials having the following preferred characteristics: lightweight, substantially rigid, inexpensive, easy to manufacture, inexpensive to manufacture and non-toxic to humans. Those skilled in the art will appreciate that a suitable material meeting these criteria is plastic. Preferably, prongs 14a, 14b and handle 12 are formed by an injection molding process, resulting in a unitary structure.

An example of how to use the apparatus for dental flossing follows. Gripper handle 36a is inserted into receptacle 16a, which is sized to provide a tight fit such that gripper handle 36a will remain therein even under tension from dental floss 38. Dental floss 38 is threaded along first channel 18a from receptacle 16a to tip 34a of first prong 14a. From tip 34a, dental floss 38 is stretched across to tip 34b of second prong 14b. At tip 34b, dental floss 38 is threaded along second channel 18b to receptacle 16b where second gripper handle 36b is inserted therein. Prongs 14a, 14b should be sufficiently flexible to permit the prongs to be squeezed towards each other to momentarily decrease the distance between tips 34a, 34b while dental floss 38 is being installed. After dental floss 38 and gripper handles 36a, 36b are inserted, prongs 14a, 14b are released, thus creating tautness on dental floss 38 across flossing section 40, which is suspended between tip 34a and tip 34b and used to floss between teeth. Cutouts 42a, 42b are provided on the lower edge of receptacles 16a, 16b adjacent first and second edge 30a, 30b, respectively of handle 12 to allow easy removal of gripper handles 36a, 36b, respectively, for replacement after use. Although dental floss 38 is typically 4 ½ inches long between gripper handles 36a, 36b, those skilled in the art will appreciate that various lengths of dental floss 38 can be used to separate gripper handles 36a, 36b, and apparatus 10 can be configured to accommodate such variations without departing from the spirit of the invention as disclosed herein.

Figure 5:
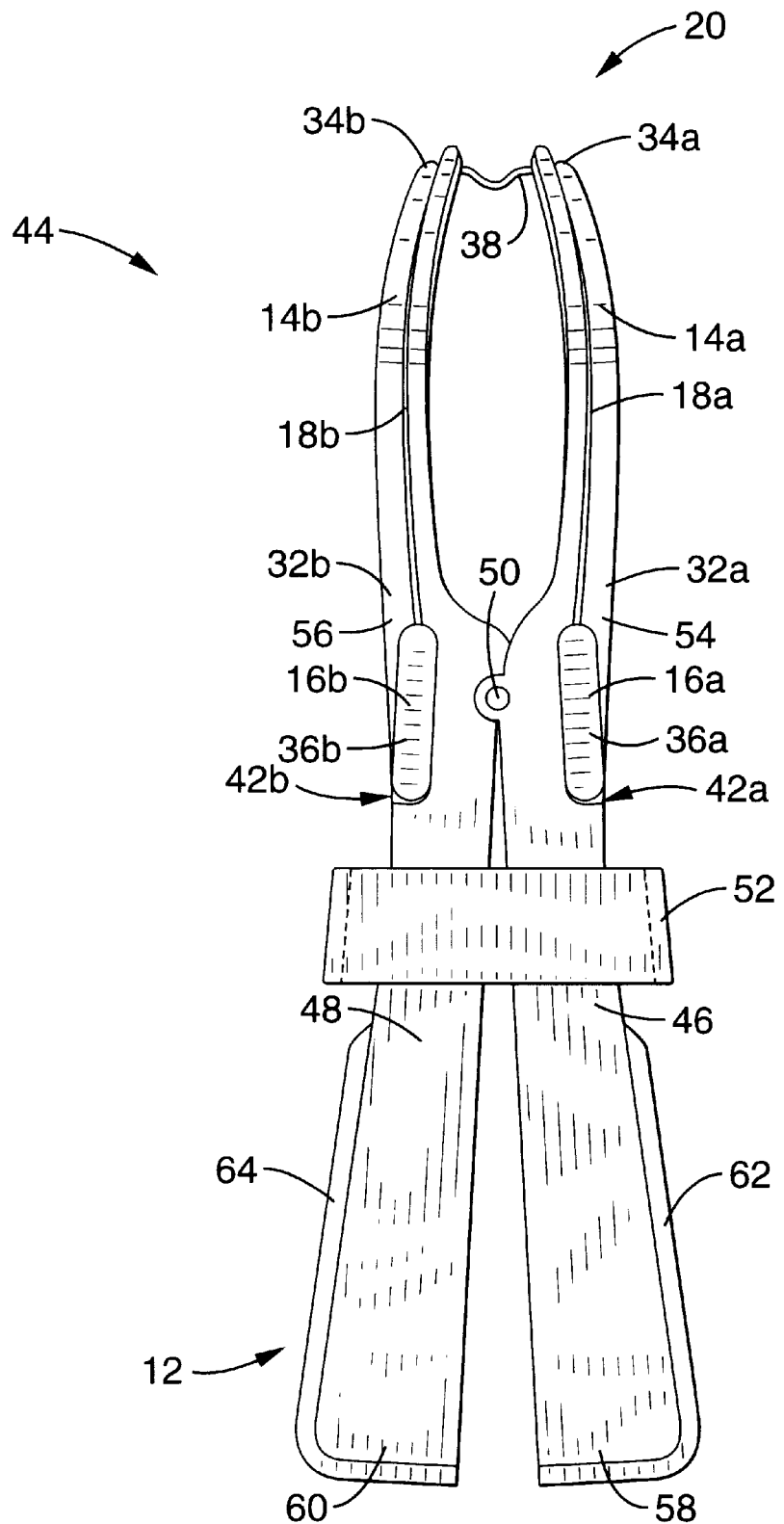
FIG. 5 is a perspective view of an alternative embodiment of the dental flossing apparatus in accordance with the present invention employing hinged handles, with the handles shown spread apart and the dental floss installed.
Figure 6:
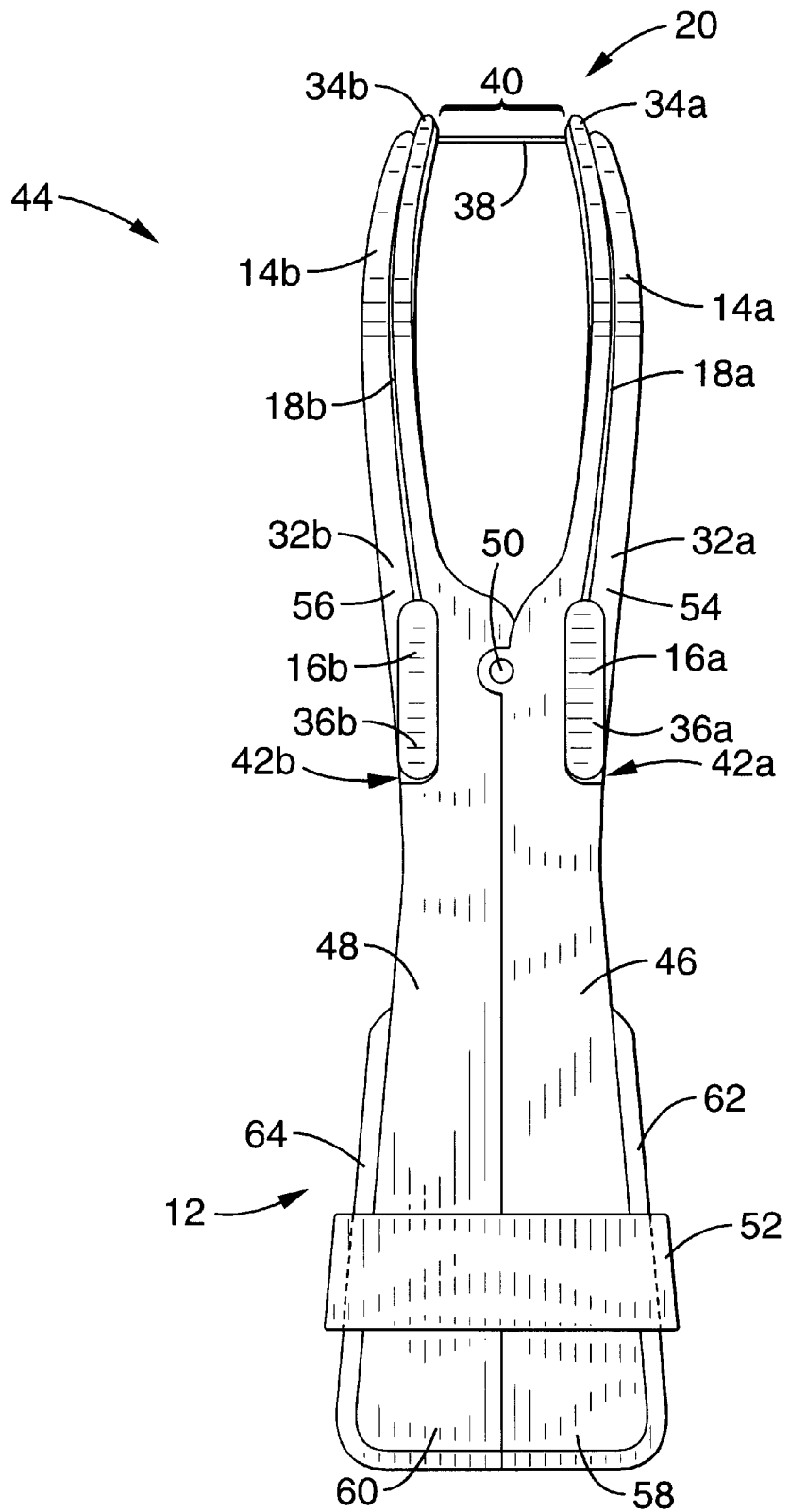
FIG. 6 is perspective view of the alternative embodiment of the dental flossing apparatus shown in FIG. 5 with the handles shown closed and the dental floss installed.

Referring now to FIG. 5 and FIG. 6, an alternative embodiment 44 of the invention is generally shown. Handle 12 in apparatus 44 comprises a pair of handle members 46, 48, first and second porngs 14a, 14b, first and second receptacles 16a, 16b, first and second channels 18a, 18b, a hinge assembly 50 and a locking band 52.

Handle members 46, 48 each include a distal end 54, 56, respectively, and a proximal end 58, 60, respectively. Handle members 46, 48 are coupled by hinge assembly 50 which allows for pivotal movement of handle members 46, 48 relative to each other. Movement of handle members 46, 48 causes a corresponding movement of prongs 14a, 14b, such that moving proximal ends 58, 60 of handles 46, 48 away from each other simultaneously causes tips 34a, 34b to move towards each other, thereby reducing the separation distance therebetween. First and second prongs 14a, 14b each has a proximal end 32a, 32b, respectively and a tip 34a, 34b, respectively, at the distal end 20 of the apparatus. Proximal end 32a of prong 14a is attached to distal end 54 of handle member 46. Similarly, proximal end 32b of prong 14b is attached to distal end 56 of handle member 48. Receptacles 16a, 16b are typically elongated as previously described and are disposed adjacent distal ends 54, 56 of handle members 46, 48, respectively. Optional grips 62, 64 are disposed around proximal ends 58, 60 of handle members 46, 48, respectively. Locking band 52 is disposed around handle members 46, 48 and serve to compress handle members 46, 48 together when locking band 52 is slid over grips 62, 64 and pushed towards proximal ends 58, 60 of handle members 46, 48, respectively. Grips 62, 64 preferably include tapered distal ends 66, 68, respectively, to assist with sliding locking band 52 into place.

An example of how to use this embodiment of the invention for dental flossing follows. Locking band 52 is slid distally off grips 62, 64 towards distal ends 54, 56 of handle members 46, 48, thereby allowing proximal ends 58, 60 of handle members 46, 48 to move away from each other and reducing the separation distance between tips 34a, 34b, as can be seen in FIG. 5. Gripper handle 36a is inserted into receptacle 16a, while gripper handle 36b is inserted into receptacle 16b. Dental floss 38 is threaded along first channel 18a from receptacle 16a to tip 34a of first prong 14a and also from receptacle 16b to tip 34b of second prong 14b. From tip 34a, dental floss 38 is stretched across to tip 34b of second prong 14b, which can readily be accomplished since the separation distance between tips 34a, 34b is temporarily reduced due to the expansion of handle members 46, 48. After the insertion of dental floss 38 as described, handles 46, 48 are compressed together to spread tips 34a, 34b apart, thereby increasing the tautness of dental floss 38 across flossing section 40 which is used to floss between teeth. Locking band 52 is then slid down over grips 62, 64 towards proximal ends 58, 60 of handles 46, 48 to maintain handle members 46, 48 in a compressed position, as seen in FIG. 6.

Because the insertion of dental floss 38 into channels 18a, 18b is facilitated by the pivoting capability of handles 46, 48, prongs 14a, 14b are preferably relatively rigid for increased tautness of dental floss 38 across flossing section 40. Cutouts 42a, 42b are provided on the proximal edge of receptacles 16a, 16b adjacent first and second edge 30a, 30b, respectively of handle 12 to allow easy removal of gripper handles 36a, 36b for replacement after use. If desired, handle members 46, 48 can be biased open (apart from each other) with a spring (not shown) or like means.

Accordingly, it will be seen that this invention eliminates the problems commonly associated with flossing teeth with the fingers while allowing use of dental floss having gripper handles at each end. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An dental flossing apparatus, comprising:
(a) a handle;
(b) a pair of elongated prongs extending from said handle, each said prong including a distal tip, said prongs inwardly flexible toward each other;
(c) a pair of receptacles, each said receptacle corresponding to one of said prongs, said receptacles adapted to receive flat, tablet-shaped gripper handles; and
(d) a channel within each said prong, each said channel extending along a prong from a corresponding receptacle to a corresponding tip.

2. An apparatus as recited in claim 1, wherein said prongs are arcuate.

3. An apparatus as recited in claim 1, further comprising a section of dental floss extending between said distal tips, said dental floss having a gripper handle at each end, each said gripper handle positioned in one of said receptacles.

4. An apparatus for flossing teeth, comprising:
   (a) a handle;
   (b) a pair of elongated arcuate prongs extending from said handle, each said prong including a proximal end and a distal tip, said prongs inwardly flexible toward each other;
   (c) a pair of receptacles within said handle, each said receptacle adapted to receive flat, tablet-shaped gripper handles, each said recptacle positioned adjacent the proximal end of the corresponding prong;
   (d) a channel within each said prong, each said channel extending from a corresponding receptacle to a corresponding tip.

5. An apparatus for flossing teeth, comprising:
   (a) a handle comprising a pair of handle members;
   (b) an elongated prong extending from each said handle member, each said prong including a distal tip;
   (c) means for pivotally coupling said handles disposed adjacent said prongs;
   (d) a pair of receptacles adapted to receive flat, tablet-shaped gripper handles, each said receptacle corresponding to one of said prongs; and
   (e) an elongated channel within each said prong, each said channel extending along a prong from a corresponding receptacle to a corresponding tip.

6. An apparatus as recited in claim 5, further comprising grips disposed around said handles.

7. An apparatus as recited in claim 5, further comprising means for locking said handles together.

8. An apparatus as recited in claim 7, wherein said locking means comprises a locking band.

9. An apparatus as recited in claim 5, wherein said receptacles are generally elongated in shape.

10. An apparatus as recited in claim 5, wherein said prongs are arcuate.

11. An apparatus for flossing teeth, comprising:
    (a) a pair of handle members;
    (b) an elongated prong extending from each said handle member, each said prong including a distal tip;
    (c) a pivot mechanism, said pivot mechanism coupling said handle members such that compressing said handles together causes said tips to spread apart from each other, wherein said pivot mechanism is disposed adjacent said elongated prongs;
    (d) a pair of receptacles adapted to receive flat, tablet-shaped gripper handles, each said receptacle positioned within a corresponding one of said handle members;
    (e) an elongated channel within each said prong extending from a corresponding receptacle to a corresponding tip; and
    (f) means for locking said handle members together.

12. An apparatus as recited in claim 11, further comprising grips disposed around said handles.

13. An apparatus as recited in claim 11, wherein said locking means comprises a locking band.

14. An apparatus as recited in claim 11, wherein said receptacles are generally elongated in shape.

15. An apparatus as recited in claim 11, wherein said prongs are arcuate.

\* \* \* \* \*